United States Patent [19]

Kronner

[11] Patent Number: 4,848,368
[45] Date of Patent: Jul. 18, 1989

[54] UNIVERSAL EXTERNAL FIXATION FRAME ASSEMBLY

[76] Inventor: Richard F. Kronner, 1443 Upper Cleveland Rapids Rd., Roseburg, Oreg. 97470

[21] Appl. No.: 185,425

[22] Filed: Apr. 25, 1988

[51] Int. Cl.$^4$ ............................................... A61F 5/04
[52] U.S. Cl. ................................................... 128/92 Z
[58] Field of Search ........... 128/92 Z, 92 ZZ, 92 ZY, 128/92 ZW, 92 Y, 92 R, 92 YE; 24/136 A; 403/61, 97, 98, 116

[56] References Cited

U.S. PATENT DOCUMENTS

| | | | |
|---|---|---|---|
| 1,627,277 | 5/1927 | Craig | 403/98 |
| 2,238,870 | 4/1951 | Haynes | 128/92 Z |
| 2,250,417 | 7/1941 | Ettinger | 128/92 Z |
| 2,251,209 | 7/1941 | Stader | 128/92 Z |
| 2,443,106 | 6/1948 | Grosso | 128/92 Z |
| 2,575,917 | 11/1951 | Johnson | 403/98 |
| 2,596,007 | 5/1952 | Casaroll | 403/98 |
| 4,733,657 | 3/1988 | Kluger | 128/92 ZZ |

FOREIGN PATENT DOCUMENTS 8302554  8/1983  World Int. Prop. O. ......... 128/2 W

Primary Examiner—Robert A. Hafer
Assistant Examiner—Michael Brown
Attorney, Agent, or Firm—Kolisch, Hartwell & Dickinson

[57] ABSTRACT

A universal external fixation frame assembly which includes a pair of rod-holder bodies adjustably mounted at spaced locations on a rod, and a pin-holder body for each rod-holder body connected to the rod-holder body through a universal swivel mechanism. The universal swivel mechanisms may be broken down to free the rod-holder bodies from the pin-holder bodies. The pin-holder bodies, with the rod-holder bodies freed therefrom, are mounted on bone segments through pins detachably mounted on and extending from the pin-holder bodies.

7 Claims, 2 Drawing Sheets

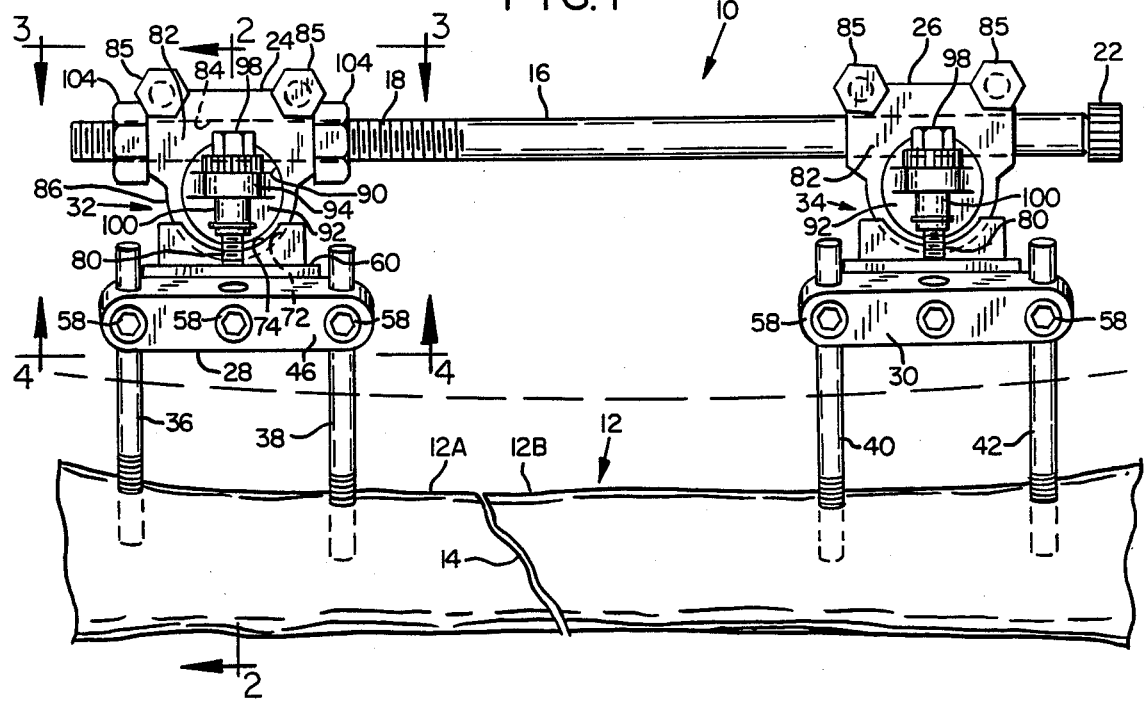
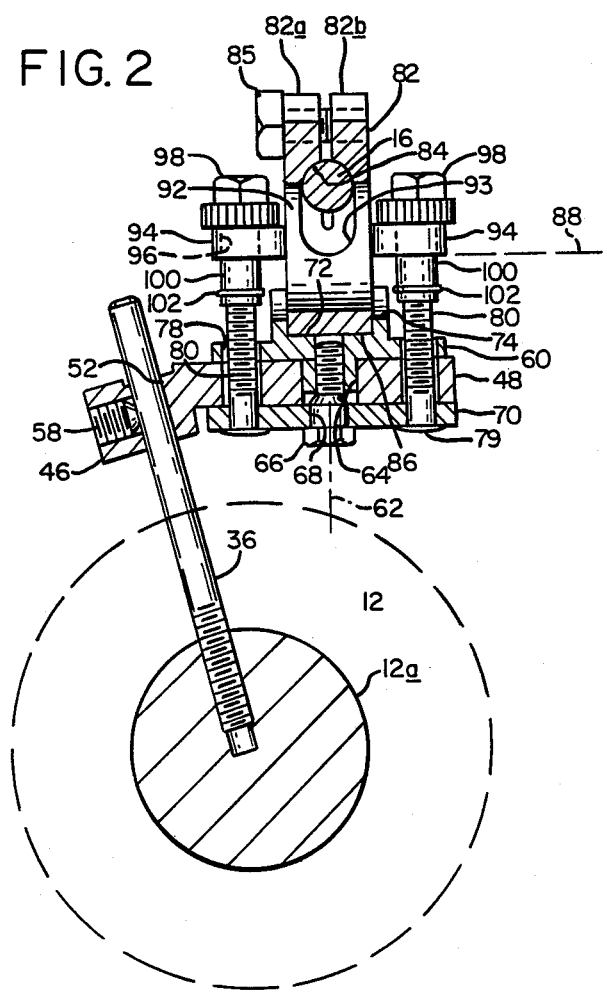
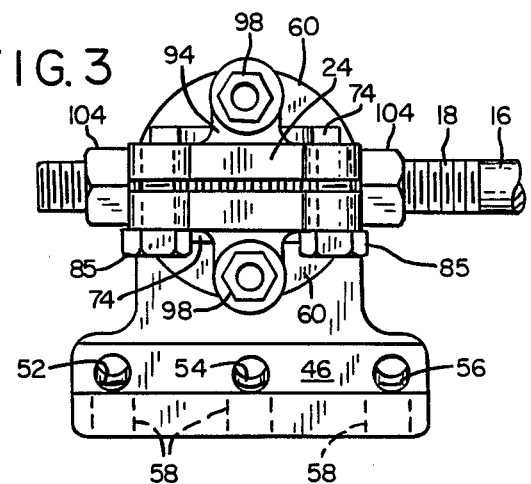
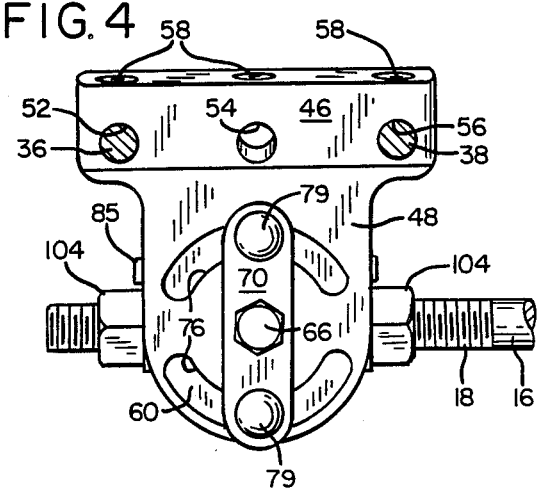

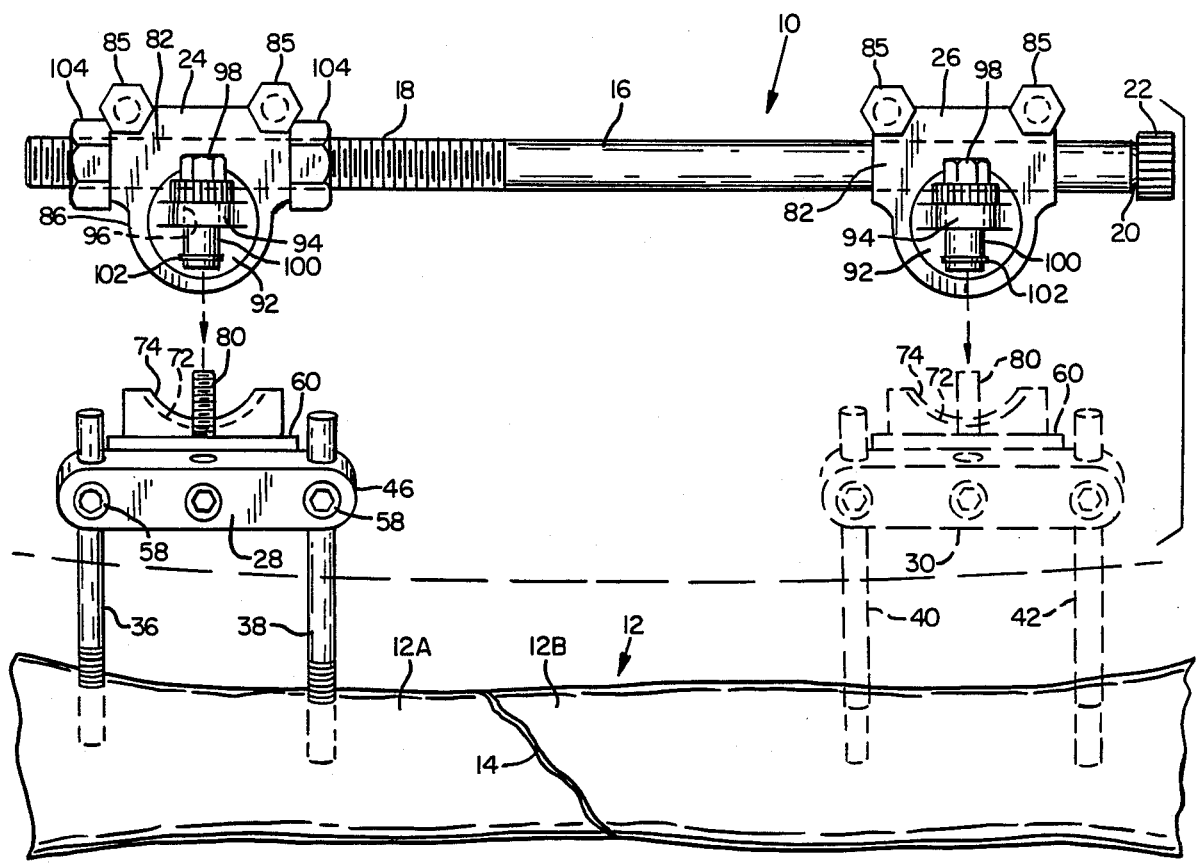
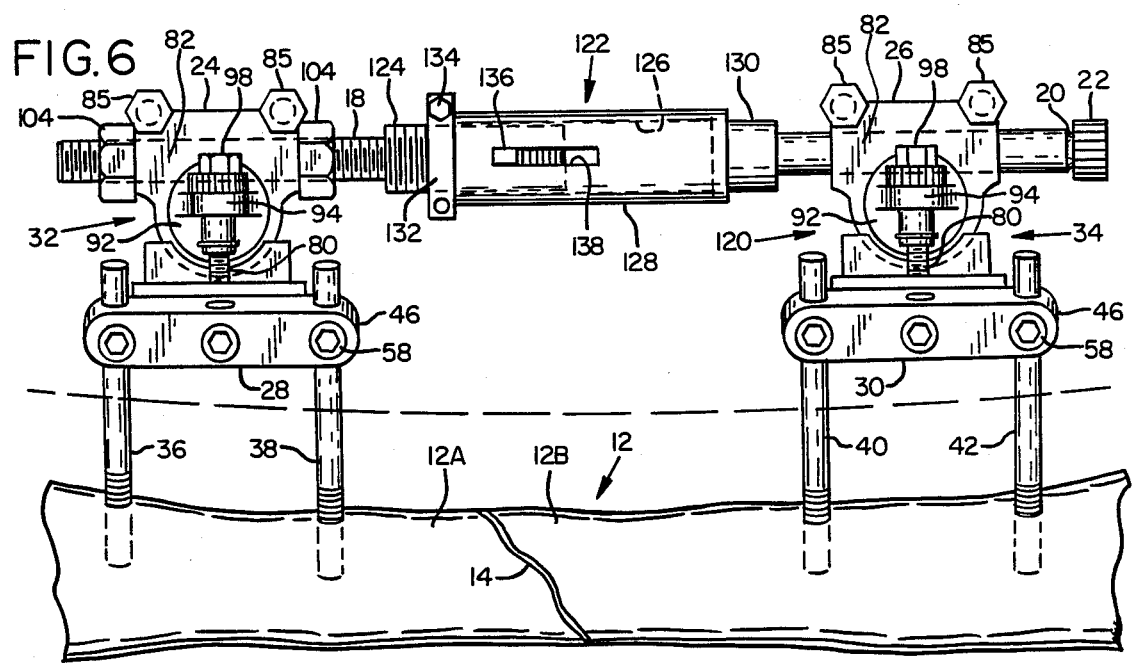

UNIVERSAL EXTERNAL FIXATION FRAME ASSEMBLY

BACKGROUND AND SUMMARY OF THE INVENTION

This invention relates to what is referred to herein as a fixation frame, and more particularly, to a fixation frame which is carried externally by a patient and which is secured as by pins to broken or fractured bone segments with the frame then functioning to hold the segments during the healing or mending process.

Fixation frames have been known in the past but have suffered from a number of disadvantages. For instance, many have been characterized by requiring a multiplicity of rods or bars interconnecting pin-holders in the frames. Such has resulted in increased bulk, and the complexity of the frames has interfered with surgical management during placement of the frames and adjustment of the bone segments interconnected by the frames. Others have lacked full adjustment capability, making adjustment of the frame difficult when assembled on the patient. Additionally, complexity in prior known construction introduces difficulties in properly assembling the frame on the patient and in subsequently tightening the various adjustable parts therein, to produce the necessary rigidity required if the bone segments attached by the frame are to be properly held.

A general object of this invention is to provide an improved external fixation frame assembly which obviates many of the difficulties characterizing prior known fixation frames.

More specifically, an object of the invention is to provide a fixation frame which includes a pair of universal mechanisms interconnecting rod-holder bodies and pin-holder bodies in the frame which are readily adjusted after placement of the frame to secure parts therein from relative swivel movement.

Another object is to provide a fixation frame with universal mechanisms, interconnecting rod-holder bodies and pin-holder bodies, which are adjustable for the purpose of disconnecting or freeing the rod-holder bodies from their respective pin-holder bodies. This enables the pin-holder bodies, with the other structure freed therefrom, to be properly attached to bone segments by the surgeon with subsequent connection of the rod-holder bodies pursuant to assembling the frame whereby the frame ultimately forms an essentially rigid structure interconnecting the bone segments involved.

The fixation frame contemplated features a minimal number of parts which are tightened together to produce rigidity in the frame after attachment of the frame and proper positioning of the bone segments being held together.

A further object is to provide, in a fixation frame of the type described, a novel construction for a universal mechanism incorporated into the frame featuring relatively extensive clamping surfaces which are adjustable to be brought against each other to then hold securely parts in the universal mechanism from relative movement.

Other objects achieved by the invention are relatively simplicity in a frame having the adjustability and functions of the frame contemplated, a construction which makes possible the elimination of loose parts in fastener systems employed, and a construction which possesses flexibility in the manner in which the frame may be connected with bone fragments, i.e., either as a single frame, a double frame in two planes, a double frame in a single plane, and a double frame in a combined single and biplane configuration.

BRIEF DESCRIPTION OF THE DRAWINGS

These and other objects and advantages are attained by the invention, which is described hereinbelow in conjunction with the accompanying drawings, wherein:

FIG. 1 is a side view of the frame assembly, with such attached through pins to a bone;

FIG. 2 is a cross-sectional view, taken generally along the line 2—2 in FIG. 1;

FIG. 3 is a view looking downwardly at an end portion of the frame assembly, taken generally along the line 3—3 in FIG. 1;

FIG. 4 is a cross-sectional view looking upwardly at a pin-holder in the assembly, and taken generally along the line 4—4 in FIG. 1;

FIG. 5 is a view similar to FIG. 1, but showing universal mechanisms in the frame assembly broken apart whereby pin-holder bodies are freed from rod-holder bodies in the frame assembly; and FIG. 6 is a view similar to FIG. 1, but illustrating a modified form of rod which may be employed in the frame assembly to provide controlled longitudinal motion in the bone segments connected by the frame assembly.

DETAILED DESCRIPTION OF A PREFERRED EMBODIMENT

Referring now to the drawings, and initially more particularly to FIG. 1, the fixation frame assembly of the invention is illustrated generally at 10, mounted on a bone 12 which has been broken at 14 to leave opposed bone segments 12A and 12B. With the fixation frame assembly mounted as illustrated, these bone segments are held by the frame assembly with the bone segments properly positioned for the mending process to proceed.

As illustrated in FIG. 1, the fixation frame assembly includes, in general terms, an elongate rod 16 having a threaded portion 18 adjacent one of its ends of substantial extent. Screwed onto the opposite end of the rod on a threaded portion 29 of minor extent is a cap 22 which functions as a retainer member. Adjustably positionable on rod 16 are a pair of rod-holder bodies shown at 24 and 26, respectively. Associated with each of the rod-holder bodies is a pin-holder body, these being shown at 28 and 30, respectively. A universal mechanism, designated at 32, detachably connects rod-holder body 24 and its associated pin-holder body 28. A similar universal mechanism 34 detachably interconnects rod-holder body 26 and pin-holder body 30. A pair of pins 36, 38 mounts pin-holder body 28 on bone segment 12A. Another pair of pins 40, 42 mounts pin-holder body 30 on bone segment 12B.

Considering now in more detail the construction of a pin-holder body, and referring to pin-holder body 28 as such is illustrated in FIGS. 1-4, such includes an elongate bar portion 46 extending along a side thereof and an ear portion 48 integrally joined to a side of bar portion 46 and extending outwardly therefrom. The ear and bar portions may occupy slightly inclined planes when viewed in cross section as illustrated in FIG. 2.

Bar portion 46 has bores 52, 54, 56 extending therethrough. These bores are utilized in the mounting of the pins which secure the pin-holder body to the bone segment, as exemplified by pins 36, 38 earlier described. The number of pins used and the particular bores employed in the mounting of the pins is a matter determined by the discretion of the surgeon applying the fixation frame assembly. Set screws, such as the one shown at 58, turnable with an Allen wrench, are employed in securing the pin-holder body to the pins with the pin-holder body occupying the desired position on the pins.

Supported on the upper surface of ear portion 48 is a swivel plate 60 which, as shown, has a substantially circular outline. The swivel plate is rotatably mounted on the ear portion, i.e., swiveled on the ear portion for movement about a swivel axis indicated at 62 in FIG. 2. More particularly, this swivel mounting is provided by a boss extending from the base of the swivel plate which is rotatably supported in a bore 64 in ear portion 48. Loosely holding the swivel plate in its place on the ear portion is a hex head screw fastener 66 with the shank thereof passing loosely through a bore 68 of a clamp bar 70 supported on the underside of ear portion 48, fastener 66 being screwed into the base of swivel plate 60.

Provided at the top of the swivel plate and as an integral part of the swivel plate is a cup-shaped bearing surface 72 which faces upwardly in FIGS. 1 and 2, this bearing surface being bounded by arcuate flange portions, such as flange portion 74. This forms part of another swivel mounting as will be described.

As best illustrated in FIG. 4, arcuate slots 76 are provided extending through ear portion 48 of the pin-holder body. A pair of screw fasteners 79 with heads appropriately secured to clamp bar 70 and with their threaded shanks extending upwardly through slot 76 and loosely through accommodating bores, such as bore 78 provided in the swivel plate, have upper threaded ends, such as end 80 (see FIG. 5) projecting upwardly on either side of bearing surface 72.

Pin-holder body 30 is constructed similarly to body 28, and like pin-holder body 28 is provided with a swivel plate, clamp bar, bearing surface, and other structure described in connection with pin-holder body 28.

Considering now the consideration of a rod-holder body, bodies 24, 26 are similar in construction and only rod-holder holder 24 will be described in detail. The rod-holder body includes a mounting portion 82 at its upper extremity which has a passage 84 extending therealong which receives rod 16. The mounting portion is split extending upwardly from passage 84 to provide opposed shoulder portions 82a, 82b (see FIG. 2). Fasteners 85 extend through these shoulder's and with tightening of these fasteners, the shoulders are brought together to cause clamping of the bar where such resides within passage 84. The axis of passage 84 and the axis of the rod when such is within the passage extends normal to and is intersected by swivel axis 62 earlier described.

Projecting downwardly from mounting portion 82 in a rod-holder body, and as shown in FIGS. 1 and 2, is a semi-cylindrically curved journal portion 86. As illustrated in FIGS. 1 and 2, the lower periphery of this journal portion seats on bearing surface 72 as retained by flanges 74. The journal portion and bearing surface provide a second swivel axis, indicated at 88 in FIG. 2, which extends transversely of and intersects swivel axis 62.

Journal portion 86 includes a central bore 90 rotatably supporting a cylindrical support member 92 which is rotatably mounted within bore 90 for rotation about swivel axis 88. The top of the support member includes an enlarged passage 93 accommodating bar 16 with the support member swiveled to different positions. Ears 94 projecting outwardly from opposite ends of the support member slidably and rotatably receive in accommodating bores 96 extending therethrough the shank portions of nut devices 98. These shank portions, shown at 100, are provided with internally threaded bores enabling the nut devices to be screwed onto the upper threaded ends 80 of fasteners 79. Ring retainers 102 prevent the nut devices from being entirely removed from the bores 96 receiving them.

With a rod-holder body mounted with its journal portion received on bearing surface of a pin-holder body and with the nut devices screwed onto the threaded ends 80 of the fasteners, but not completely tightened, the rod-holder body can swivel on the pin-holder body and through swivel plate 60 about swivel axis 62. Furthermore, the rod-holder body can swivel about swivel axis 88 relative to the swivel plate. Thus, the structure described provides a universal swivel connection between the rod-holder body and the pin-holder body. With the nut devices turned to tighten them completely on the threaded portions 80, clamp bar 70 is drawn upwardly in FIG. 2 toward ears 94 and with the nut devices completely tightened, ear portion 48 of a rod-holder body becomes tightly clamped between the under surface of the swivel plate on one side and the upper surface of the clamp bar on its opposite side. This effectively prevents swivel movement about axis 62. Furthermore, journal portion 86 of the rod-holder body is drawn tightly downwardly against bearing surface 72 on the upper side of the swivel plate to prevent relative movement between the journal portion and bearing surface and relative swivel movement of the rod-holder body relative to the pin-holder body about swivel axis 88. Loosening of the nut devices releases this clamping pressure, and on complete loosening and freeing of the nut devices from portions 80, the universal mechanism, in effect, may be broken apart as shown in FIG. 5 to leave the pin-holder body and the swivel plate as one assembly and the rod-holder body and its journal portion as a separate assembly.

It will be noted, and with reference to FIG. 1, that mounting portion 82 of rod-holder body 26 envelops a smooth surfaced portion of rod 16. Coarse adjustments of the rod-holder body with respect to the rod are produced by loosening fasteners 85 so that the rod-holder body becomes relatively rotatable on and also axially shiftable along the length of rod 16. With the rod-holder body in a desired position, fasteners 85 may be tightened to anchor the rod-holder body in the position. Mounting portion 82 of rod-holder body 24, on the other hand, envelops the threaded portion 18 of rod 16 and the mounting portion is abutted at opposite ends by nuts 104 screwed onto this threaded portion. This permits fine adjustments to be made in this rod-holder portion without loss of distraction. For instance, and with fasteners 85 of this rod-holder loose, the left hand nut 104 may be turned to move it to the left on the threaded part 18 of rod 16. The right hand nut 104 may then be turned whereby it also moves along the rod and toward the left with pushing of the rod-holder body in front of it. With a finely adjusted position of the rod-holder body attained, fasteners 85 are tightened to clamp the rod-holder body in place.

Describing how the fixation frame may be used, and with reference to FIG. 5, the pin-holder bodies and their associated swivel plates may first be removed from the remainder of the apparatus through unscrewing nut devices 98 to free them from threaded ends 80. Pin-holder body 28 may then be positioned over one bone segment and pins inserted through the pin-holder body and into the bone segment as exemplified by the pins 36, 38. Pin-holding set screws 58 are then tightened to secure the pin-holder body on the pins.

Pin-holder body 30 may then be secured to the other bone segment utilizing a similar procedure. Fasteners 85, i.e., the rod-locking screws, associated with the two rod-holder bodies, are loosened. This permits both rod-holder bodies to be rotated on rod 16 and rod-holder body 26 also to be shifted freely in an axial direction. With this condition of the parts, the journal portions of the rod-holder bodies are fitted into the respective bearing surfaces 72 provided in the pin-holder bodies. The rod-holder bodies are then connected to the pin-holder bodies through screwing nut devices 98 onto the appropriate ends 80 of the fasteners in the pin-holder bodies.

With the universal mechanisms interconnected, fasteners or rod locking screws 85 for the rod-holder body which encircles the smooth surface of rod 16 are tightened, to secure this rod-holder body in place on the rod. If it is desired to apply distraction at this point, nuts 104 are rotated to advance rod-holder body 24 the extent desired along rod 16 and away from rod-holder body 26.

The bone segments in the fractured bone may then be manipulated appropriately to produce proper alignment, and this manipulation may include producing relative rotational movement in the segments, shifting of the relative angularity, and shifting of their offset. If desired, compression may then be applied by a rotation of the nuts 104 with advancing of body 24 toward body 26. With all parts properly positioned, all rod-locking screws and nut devices 98 are tightened, which serves to make the fixation frame completely rigid.

A double frame configuration may also be produced utilizing the fixation frame assembly. And this configuration may either be in a biplane configuration, or in a single plane configuration, or in a configuration which combines a single and a biplane configuration. In producing a double plane configuration, two frame assemblies of the type above described are secured to the bone segments, the mounting of each frame assembly being accompanied with first mounting of the pin-holder bodies and subsequent attachment of the universal mechanisms whereby the rod-holder bodies become connected with the pin-holder bodies. If increased rigidity is desired, and where two fixation frame assemblies are employed in the setting of a fractured or broken bone, cross rods may be added to extend between and connect the rods of the respective fixation frame assemblies.

FIG. 6 illustrates a modification of the invention, wherein rod 16 is replaced with a rod 120 having a longitudinal motion accommodating device 122 incorporated between its threaded and smooth surfaced ends. Considering in more detail device 122, threaded end 18 of the rod extends to joinder with a threaded portion 124 of somewhat larger diameter. This threaded portion is slidably received within the hollow interior 126 of a cylinder 128 which has its opposite end unified and through step portion 130 with the smooth surfaced end of the rod. Shown at 132 is a collar with internal threads which is screwed onto threaded portion 124 and abuts the ends of cylinder 128. Shown at 134 is a locking screw which is tightened to secure the collar in place on threaded portion 124. A pin 136 joined to threaded portion 124 and extending out through a slot 138 in cylinder 128 holds threaded portion 124 from rotating with respect to cylinder 128 while accommodating relative longitudinal movement of the threaded portion within the cylinder.

In utilizing the device and in setting up the fixation frame, locking screw 134 is loosened and collar 132 rotated on threaded portion 124 until pin 136 is up against the end of the slot 138 adjacent the collar. The collar's position is then fixed by tightening locking screw 134.

If limited relative longitudinal movement in the setting bone fracture is desired, to assist in callous formation or other reasons, at some time interval after initial placement of the fixation frame, the locking screw is loosened to free the collar for rotation on threaded portion 124. The collar is then turned on threaded portion to advance it the desired degree toward the left in FIG. 6 on the threaded portion. With the final desired position for the collar, the set screw is retightened. A pitch of the thread may be selected so that for one complete rotation of the collar, one millimeter of motion is provided in the rod extremities interconnected by device 122.

It should be apparent from the above that a relatively simple but extremely versatile fixation frame has been described. In the fixation frame, only a single rod extends between the rod-holding bodies which are supported in the assembly. These are relatively rotatable when loose on the rod and also are relatively adjustable in a direction extending axially of the rod, with adjustment in an axial direction being both in a coarse mode and in a fine mode. The universal mechanisms described swivel about two axes to permit assembly of the fixation frame in the position desired. The pin-holder bodies are attachable to the bone using the pins, with the rod-holder bodies freed from the pin-holder bodies. The pin-holder and rod-holder bodies are united and also clamped in adjusted positions utilizing the fastener system, including nut devices 98 journaled on support member 92 and the threaded fastener extremities which extend upwardly from the swivel plate on either side of the bearing surface which receives the journal portion.

While a particular embodiment of the invention has been described together with a modified form of connecting rod mounting the rod-holder bodies, obviously other modifications and variations are possible without departing from the invention.

I claim:

1. A universal external fixation frame assembly comprising:
   an elongate rod,
   a pair of rod-holder bodies disposed in spaced locations on said rod, said rod-holder bodies being relatively adjustably positionable rotatably on said rod and also in a direction extending axially on said rod,
   a pin-holder body associated with each rod-holder body, and
   a universal swivel mechanism interconnecting each rod-holder body with its associated pin-holder body, each universal swivel mechanism including a swivel plate swiveled on said pin-holder body for swivel movement about one swivel axis extending perpendicular to the swivel plate, and swivel means interconnecting the swivel plate and the rod-holder body including a swivel journal portion on the rod-holder body and a swivel bearing portion on said swivel plate providing for swivel movement of the rod-holder body relative to the swivel plate about another swivel axis extending perpendicular to said one swivel axis, said swivel bearing portion having a cylindrical curvature curving about an axis corresponding to said other swivel axis and being cup-shaped to accommodate freeing of the journal portion by shifting of the journal portion in a direction extending laterally of said other swivel axis, and holding means operatively interposed between the swivel plate and rod-holder body holding the journal portion in a position seated in said bearing portion, said holding means including detachable fastener means and said fastener means being adjustable to free the rod-holder body from its associated pin-holder body by separating the swivel journal portion from said swivel bearing portion on said swivel plate.

2. The fixation frame of claim 1, wherein said adjustable means further includes clamp means holding to produce clamping of the swivel plate against the pin-holder body and to clamp said swivel journal portion against said swivel bearing portion, thus to restrain pivotal movement about said swivel axes.

3. A universal external fixation frame assembly comprising:
   an elongate rod,
   a pair of rod-holder bodies disposed in spaced locations on said rod, said rod-holder bodies being relatively adjustably positionable rotatably on said rod and also in a direction extending axially on said rod,
   a pin-holder body associated with each rod-holder body, and
   a universal swivel mechanism interconnecting each rod-holder body with its associated pin-holder body, each universal swivel mechanism including a swivel plate swiveled on said pin holder body for swivel movement about one swivel axis extending perpendicular to the swivel plate, a cup-shaped swivel bearing portion joined to the swivel plate and facing outwardly thereon, a swivel journal portion formed as an integral part of said rod-holder body seating in said swivel bearing portion and movable in the swivel bearing portion about a second swivel axis extending perpendicular to the one swivel axis, and holding means operatively interposed between the swivel plate and rod holder body holding said journal portion in a position seated in said bearing portion.

4. The fixation frame of claim 3, wherein said holding means comprises a support member rotatably mounted on said rod-holder body for rotation about said second swivel axis, a clamp plate mounted for rotation on said pin-holder body, and detachable means extending between said interconnecting said support member and said clamp plate.

5. The combination of a rod-holder body and a pin-holder body and universal swivel mechanism interconnecting the two bodies accommodating relative swiveling of the bodies about a pair of swivel axes extending transversely of each other,
   said swivel mechanism comprising a mounting ear integral with the rod-holder body,
   a swivel plate swiveled on said mounting ear for swivel movement about one of said swivel axes,
   a cup-shaped swivel bearing portion joined to the swivel plate and facing outwardly thereon,
   a swivel journal portion integral with the rod-holder body seated in the swivel bearing portion and rotatable while seated relative to the bearing portion about the other of said swivel axes, the cup-shaped swivel bearing portion curving about an axis corresponding to said other swivel axis,
   a support member rotatably mounted on said swivel journal portion for rotation about said other swivel axis, and
   detachable fastener means mounted on said support member operatively interconnecting the support member and swivel plate and maintaining said journal portion seated in said bearing portion.

6. The combination of claim 5, wherein said swivel plate is disposed on one side of said mounting ear and which further includes a clamp plate disposed on the other side of said mounting ear, said fastener means connecting with said clamp plate and on adjustment of the fastening means drawing the clamp plate toward the support member to cause clamping of the journal portion against the bearing portion and clamping of the swivel plate against said ear.

7. The combination of claim 6, wherein said rod-holder body has a mounting portion with a passage extending therethrough adapted to receive a rod with the rod slidably and rotatably mounted in said mounting portion, said passage positioning said rod with the axis of the rod extending transversely of said other swivel axis and with said one swivel axis normal to and intersecting the axis of the rod.

* * * * *